(12) United States Patent
Webster

(10) Patent No.: US 8,988,677 B2
(45) Date of Patent: Mar. 24, 2015

(54) CUVETTE AND OPTICAL METHOD

(75) Inventor: Simon Webster, West Yorkshire (GB)

(73) Assignee: Avacta Limited (GB)

( * ) Notice: Subject to any disclaimer, the term of this patent is extended or adjusted under 35 U.S.C. 154(b) by 564 days.

(21) Appl. No.: 13/265,969

(22) PCT Filed: Apr. 23, 2010

(86) PCT No.: PCT/GB2010/050661
§ 371 (c)(1),
(2), (4) Date: Jan. 10, 2012

(87) PCT Pub. No.: WO2010/122346
PCT Pub. Date: Oct. 28, 2010

(65) Prior Publication Data
US 2012/0099098 A1  Apr. 26, 2012

(30) Foreign Application Priority Data

Apr. 23, 2009  (GB) .................................. 0906986.5

(51) Int. Cl.
*G01N 1/10*  (2006.01)
*G01N 21/03*  (2006.01)
(52) U.S. Cl.
CPC ............ *G01N 21/03* (2013.01); *G01N 21/0332* (2013.01); *G01N 2201/0446* (2013.01); *G01N 2021/0346* (2013.01)
USPC ....................................................... 356/246
(58) Field of Classification Search
CPC .............. G01N 2201/0446; G01N 2021/0357; G01N 21/0303; G01N 2021/0396; G01N 21/07
USPC .......... 356/246, 244, 38–42, 243.2, 432–436, 356/336–339, 440–442
See application file for complete search history.

(56) References Cited

U.S. PATENT DOCUMENTS 3,573,470 A * 4/1971 Haley ............................ 250/575
3,582,218 A * 6/1971 Anderson ..................... 356/427
(Continued)

FOREIGN PATENT DOCUMENTS

DE          3108474 A1    9/1982
DE     102005062910 A1    7/2007
(Continued)

OTHER PUBLICATIONS

International Search Report regarding PCT/GB2010/050661 issued Sep. 22, 2010, 15 pages.
(Continued)

*Primary Examiner* — Michael A Lyons
*Assistant Examiner* — Shawn Decenzo

(57) ABSTRACT

A unit is provided comprising an array (2) of sample containers (1), said containers, being connected together and arranged in a planar configuration, each container having multiple optically transparent windows arranged such that the sample contained therein can be interrogated using simultaneous multiple optical analytical techniques, the array of containers being configured so as to allow optical access to the windows of each container in the array. Also provided is an apparatus comprising such a unit, a system comprising a combination of such an apparatus and unit and a method of analyzing multiple samples by introducing each individual sample into an individual container of such an apparatus, illuminating the samples and detecting and analyzing light emerging therefrom.

28 Claims, 11 Drawing Sheets

(56) References Cited

U.S. PATENT DOCUMENTS

| | | | |
|---|---|---|---|
| 3,695,772 A * | 10/1972 | Spyropoulos | 356/246 |
| 3,724,957 A * | 4/1973 | Tamate et al. | 356/367 |
| 3,854,050 A * | 12/1974 | Peterson et al. | 250/429 |
| 3,873,217 A * | 3/1975 | Anderson et al. | 356/246 |
| 4,226,531 A | 10/1980 | Tiffany et al. | |
| 4,443,104 A * | 4/1984 | Ringhardtz | 356/246 |
| 4,720,465 A * | 1/1988 | Jensen et al. | 436/523 |
| 4,787,744 A * | 11/1988 | Hissung | 356/246 |
| 4,828,386 A * | 5/1989 | Matkovich et al. | 356/246 |
| 4,895,706 A * | 1/1990 | Root et al. | 422/534 |
| 5,254,479 A * | 10/1993 | Chemelli | 436/180 |
| 5,756,292 A | 5/1998 | Royer | |
| 5,835,231 A * | 11/1998 | Pipino | 356/440 |
| 6,768,122 B2 * | 7/2004 | Dong et al. | 250/458.1 |
| 6,777,244 B2 * | 8/2004 | Pepper et al. | 436/165 |
| 7,202,945 B2 * | 4/2007 | Erlbacher et al. | 356/246 |
| 7,527,975 B2 * | 5/2009 | Fischer et al. | 436/60 |
| 7,527,977 B1 * | 5/2009 | Fruetel et al. | 436/180 |
| 2013/0286381 A1 * | 10/2013 | Some et al. | 356/72 |

FOREIGN PATENT DOCUMENTS

| | | |
|---|---|---|
| EP | 1524514 A1 | 6/2003 |
| WO | 2004026475 A1 | 4/2004 |

OTHER PUBLICATIONS

Search Report regarding Application No. GB0906986.5 issued Jun. 23, 2009, 1 page.

* cited by examiner

Figure 2:
2.1
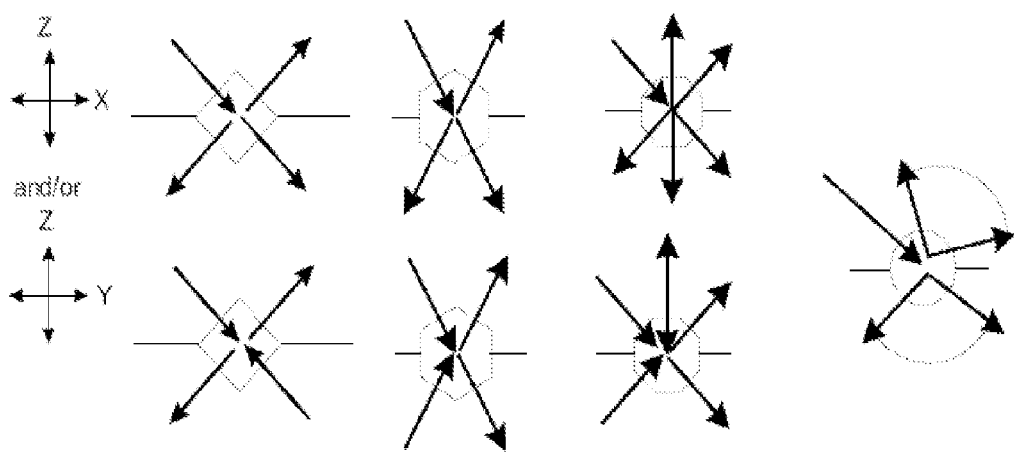
2.2
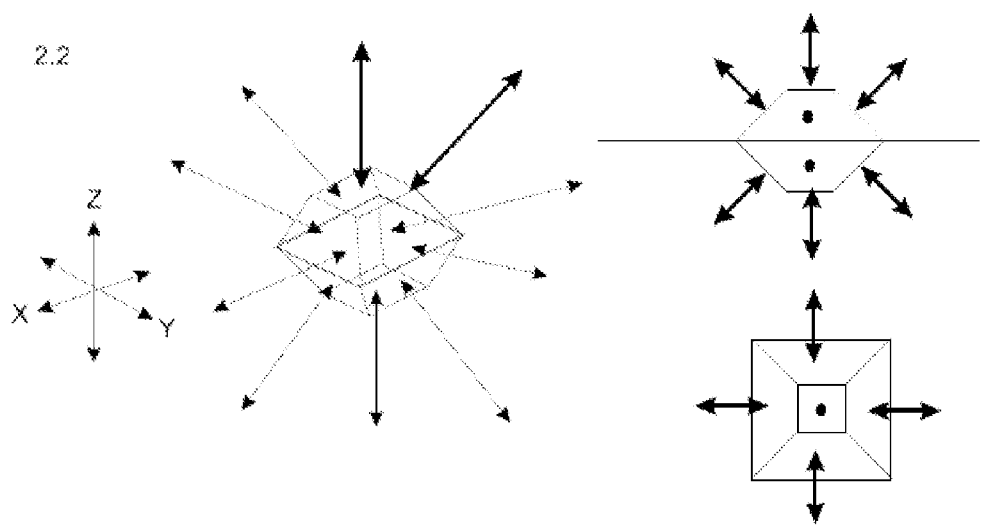
2.3
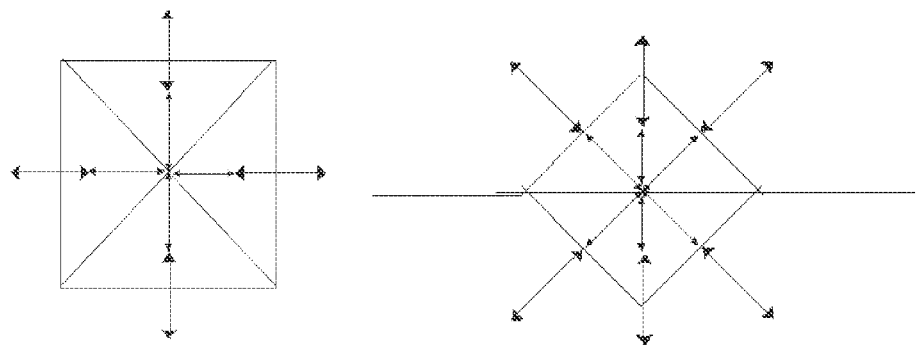

4.1

4.2

Figure 5:
5.1
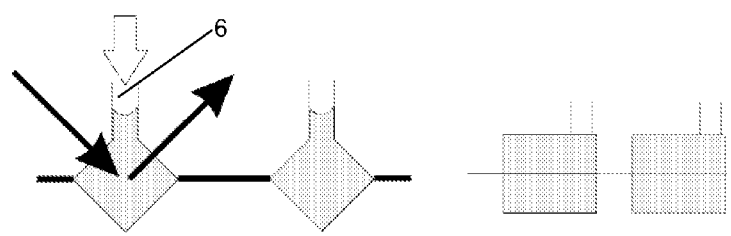
5.2
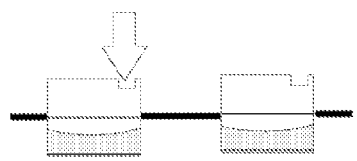
5.3
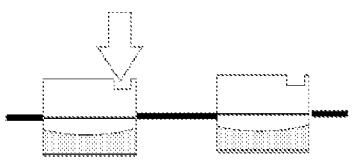
ii)
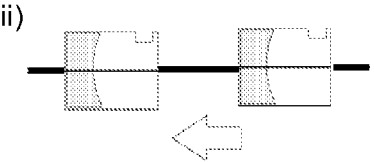
iii)
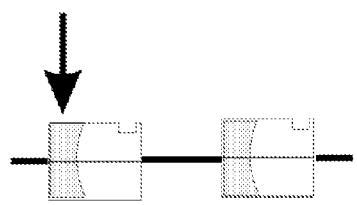
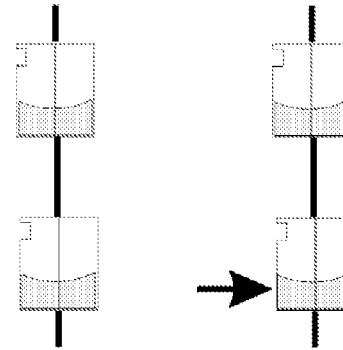

Figure 6:
6.1
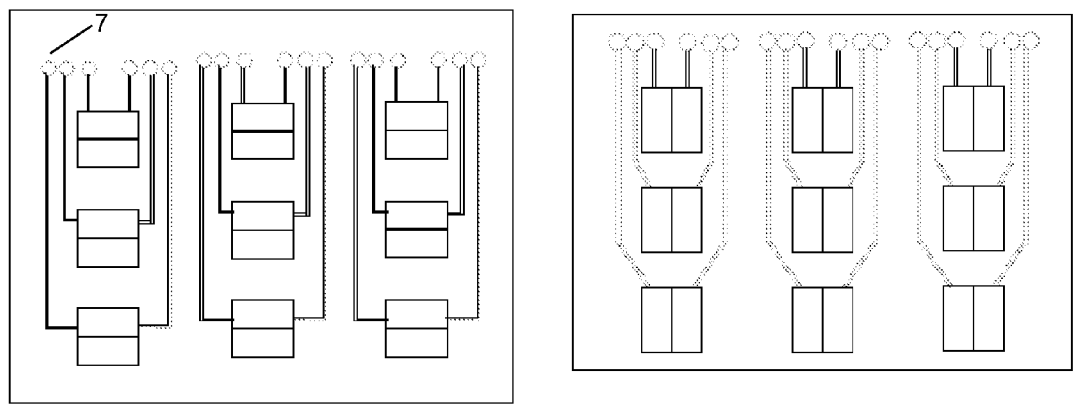
6.2
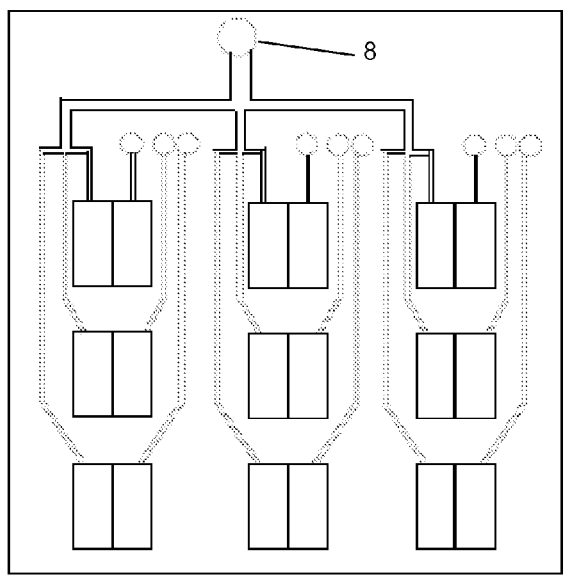

Figure 7:
7.1
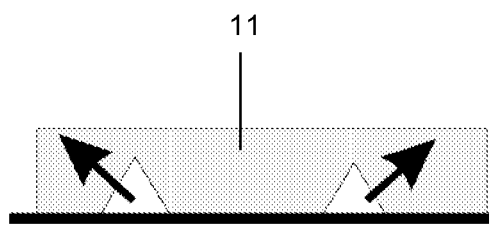
7.2
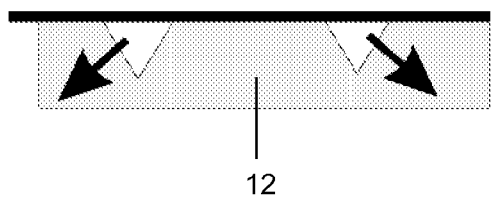
7.3
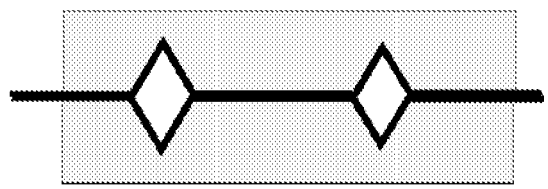
7.4

Figure 8:
8.1
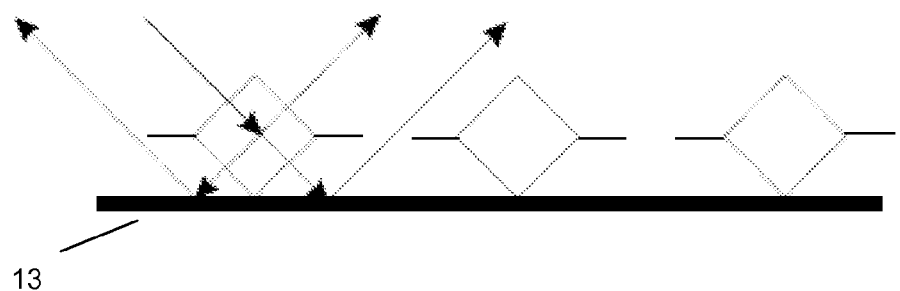
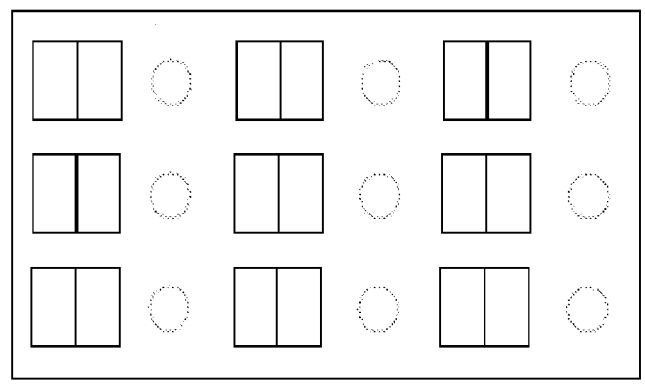
8.2
(a)
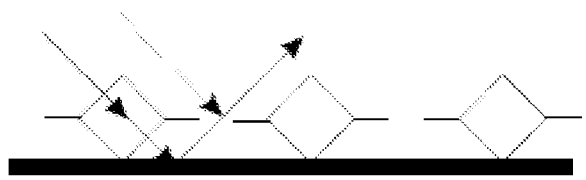
(b)
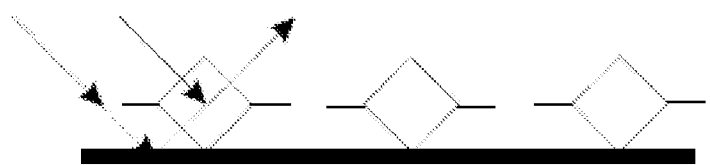

Figure 9:
9.1
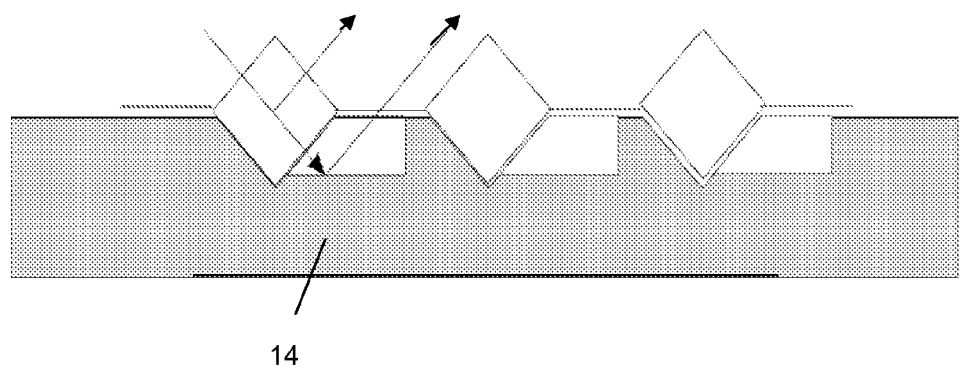
14
9.2
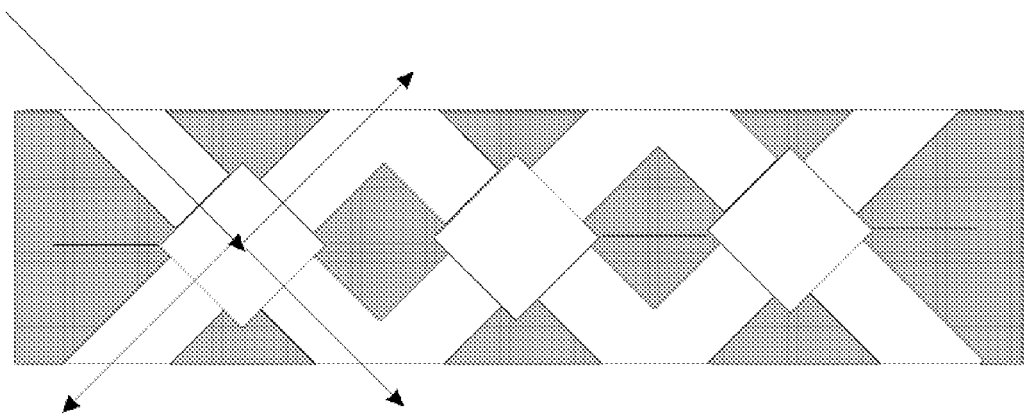

Figure 11:
11.1
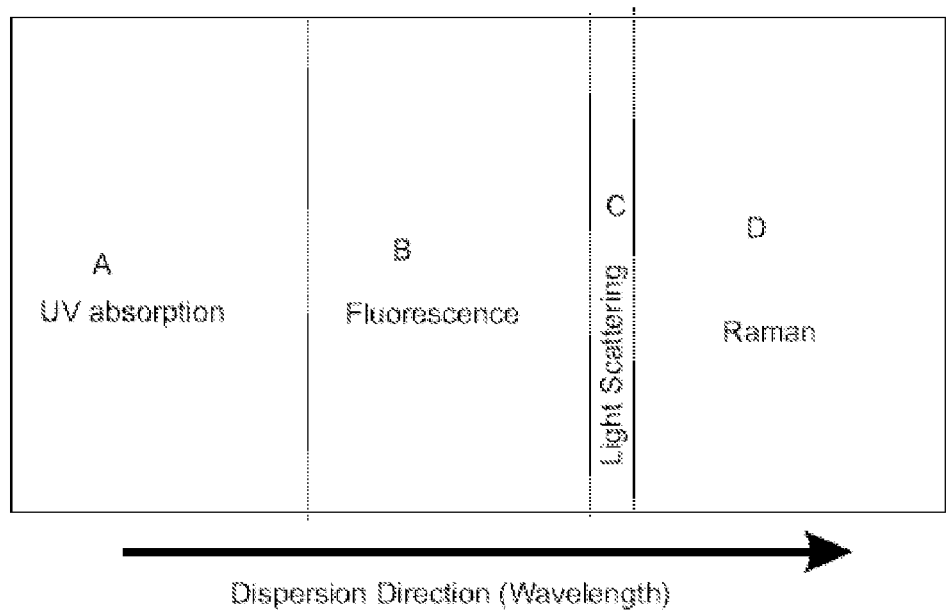
11.2
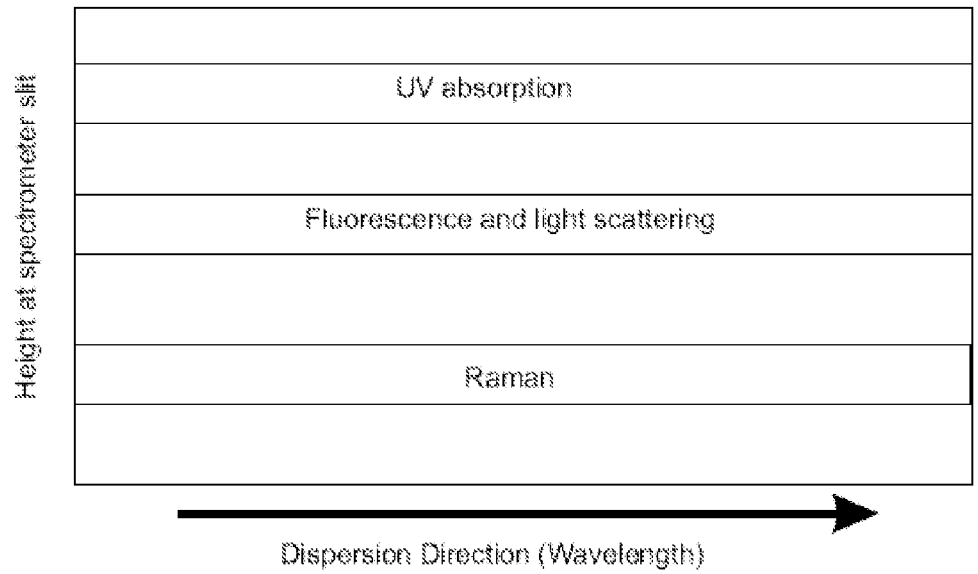

CUVETTE AND OPTICAL METHOD

FIELD OF THE INVENTION

The present invention relates to apparatus, and systems for allowing multiple types of different optical measurement to be made simultaneously from a sample to provide information about the sample as well as to units for use in such apparatus and systems and methods for analysis using such apparatus and units. In particular, the invention relates to apparatus, units and systems for use in the simultaneous acquisition of multiple different types of optical analytical measurements from an array of samples.

BACKGROUND OF THE INVENTION

A range of analytical techniques employing optical means are available to provide information about substances of interest. Typically, the sample of interest is illuminated with light and, depending on the technique employed, the resulting emitted, scattered or transmitted light is collected, spectrally analysed as appropriate and then detected using some form of optical detector.

Optical analytical techniques in common use include fluorescence spectroscopy, optical absorption spectroscopy, infra-red absorption spectroscopy, light scattering and Raman spectroscopy.

Each form of optical analytical technique can provide different information about a substance of interest and it is therefore often advantageous to perform multiple different forms of optical analysis on a given sample in order to provide a deeper understanding of the sample's properties.

A range of containers are available to allow the performance of individual optical measurements from single liquid samples and these are generally described as 'cuvettes'. Different designs are generally used for different optical measurement techniques although in principle a simple square cross section cuvette with four transparent walls could be used for multiple optical analytical techniques. Heating/cooling blocks are available to control the temperature of conventional cuvettes. Although cuvettes are available for a wide range of sample volumes, these sample volumes are generally larger than 50-100 µl, although special cuvettes are available that in favourable circumstances can use as little as 12 µl.

Widely used multi-container arrays are 96 well, 384 well and 1536 well 'micro-titre' plates conforming to standards published by the Society for Biomolecular Screening. These can be either viewed from the top or in some cases through the bottom of the well. These sample plates do not however allow illumination and collection of light at a wide range of angles and thus the optimum configuration for many of the optical analytical techniques can not be achieved. Although it is possible to perform a range of optical analytical techniques in these plates, therefore, the sample volumes generally have to be relatively large to compensate for the sub-optimal optical configuration.

A particular problem arises when optical absorption measurements are performed in standard micro-titre plates due to the optical path length being affected by both sample volume and meniscus affects which can lead to inaccurate measurements. While standard micro-titre plates can be heated and cooled their design makes the simultaneous application of multiple optical analytical techniques difficult. Real time polymerase chain reaction (RT-PCR) thermo cyclers represent the current state of the art in multi-well sample temperature control however these only allow visible fluorescence measurements and the lack of an optimised excitation-collection geometry requires that large sample volumes are required.

There are a wide range of spectrometers and light scattering instruments available that perform a single type of optical analysis on one sample at a time. Examples include fluorescence spectrometers exemplified by the RF-5301PC from Shimadzu, optical absorption spectrometers as exemplified by UV-2450PC from Shimadzu and light scattering instruments exemplified by the Zetasizer Nano™ from Malvern instruments, Raman spectrometers exemplified by the InVia™ spectrometer from Renishaw plc and circular dichroism (CD) spectrometers exemplified by the J-815 spectrometer from Jasco and the Chirascan™ spectrometer from Applied Photophysics. Generally the instruments described above can only record a single type of optical analytical data from a single sample. The CD spectrometers from JASCO and Applied Photophysics can, however, be modified to also acquire optical absorption and basic fluorescence intensity measurements although, again, these are only suitable for single sample cuvettes. Motorized sample changers are available for some instruments which typically hold up to 6 individual cuvettes.

Spectrometers and that perform a single type of measurement sequentially on multiple samples in SBS standard micro-titre plates in an automated fashion are also available. These are exemplified by the Spectramax™ 190 and the Spectramax Gemini™ spectrometer from Molecular Devices.

Instruments are available that are compatible with the SBS standard micro-titre plates described above that enable both fluorescence and optical absorption measurements to be made in the same instrument. Examples include the Infinte™ 200 from Tecan. Typically these illuminate and collect from either above or below the samples which presents various problems for the different measurement types. For example, problems occur in optical absorption measurements due to meniscus effects and path length dependence on the sample volume. Problems increase as the sample volumes are reduced.

A disposable multi-cuvette rotor is disclosed in U.S. Pat. No. 4,226,531 in which the sample cells are arranged in a radial configuration with the cells lying at the circumference of the disc. Although in this configuration, the cells can have three optical windows, potentially allowing both optical absorption and fluorescence or light scattering measurements to be made, no such applications are described and indeed the device as described would not lend itself to being used to perform simultaneous multiple optical measurements. Not only does the radial configuration of cells limit the total number of cells which can be accommodated in a given sample plate but it also limits optical access to only three optical windows. Moreover, as the liquid sample does not contact all three optical windows, optical absorption measurements are therefore potentially subject to errors due to differences in sample depth and meniscus effects.

In a number of important applications, such as protein thermal stability measurements, samples are available in only very small quantities and are not re-usable between tests which can prevent the separate application of multiple optical measurements. It would therefore be advantageous if multiple types of optical analysis could be performed simultaneously on small sample volumes. In addition simultaneously performing multiple analytical measurements from the same sample volume could potentially speed up measurements from large numbers of samples in applications such as high throughput screening.

As sample volumes decrease it becomes increasingly important to collect scattered, emitted or transmitted light from the sample with as high efficiency as possible and this is best achieved by using high numerical aperture optics. However, existing arrayed sample containers such as the widely used 96-well plates, restrict optical access to the sample volume, impairing the efficiency of the light collection.

Each of the different optical analysis methods has its own optimum geometric configuration for illumination and collection of the light in which can the signal to noise ratio of the acquired data is improved. As sample volumes are reduced the need to optimise the optical configuration becomes increasingly important since the amount of desirable signal decreases with sample volume whilst unwanted interference due to scattering or auto-fluorescence from the container increases. A sample container that allows the optimum optical configuration to be simultaneously maintained for multiple analytical methods would therefore be advantageous.

In addition in many applications it is desirable to be able to sequentially analyse multiple samples in an automated fashion in order that more experiments may be performed with in less time and with less dependence on human expertise.

Another common requirement for many biochemical and other applications is the facility to control the temperature of samples as they are analysed. It would therefore be desirable for any array of sample containers to be compatible with efficient heating and cooling of the sample during the application of multiple optical analytical techniques.

Moreover, in many applications it is desirable to have sample containers that are cheap enough to be disposable due to the cost and difficulty of effective cleaning.

As is apparent from the above discussion, there therefore remains a continuing need for the development of an improved system for obtaining multi-modal optical measurements from multiple samples, in particular which allows for the analysis to be carried out rapidly and automatically, suitably in high through-put manner.

SUMMARY OF THE INVENTION

In a first aspect, the invention provides a unit comprising an array of sample containers, said containers being connected together and arranged in a planar configuration, each container having multiple optically transparent windows arranged such that the sample contained therein can be interrogated using simultaneous multiple optical analytical techniques, the array of containers being configured so as to allow optical access to the windows of each container in the array.

In another aspect, the inventor provides an apparatus for carrying out simultaneous multiple optical analytical techniques on a sample, said apparatus comprising means for receiving a unit as described above, means for illuminating a sample contained in said unit and means for detecting light emerging from said sample.

In a further aspect, the invention also provides a system for carrying out multiple optical analytical techniques simultaneously, said system comprising a combination of a unit and apparatus as described above.

The invention also provides a method of analysing multiple samples by introducing each individual sample into an individual container of an apparatus according to the invention, illuminating the samples and detecting light emerging therefrom.

By using a unit according to the invention, problems experienced commonly in existing multi-container arrays resulting from meniscus effects and variable path lengths due to different sample volumes may be avoided. The unit may conveniently be loaded using existing fluid handling systems and may readily be fabricated from low cost materials, allowing it to be disposable. In combination with a system of optical components to allow light from multiple different light sources to be directed through one or more windows of each sample container, the apparatus allows multiple different optical analytical methods to be simultaneously applied to small sample volumes whilst maintaining the optimum optical configuration for each of these analytical methods, allows simultaneous illumination of the sample from multiple angles and also simultaneous collection of emitted, scattered or transmitted light from the sample at multiple angles.

BRIEF DESCRIPTION OF THE DRAWINGS

FIG. 1.3 shows side and plan views of a conventional micro-titre plate;

FIG. 2 shows cross-sectional views of containers suitable for use in the unit and apparatus of the invention illustrating multiple optical windows and multiple possible optical paths in and out of the container;

FIGS. 3.2 and 3.3 illustrate schematically the delivery and collection of light from a conventional micro-titre plate, with one light delivery and collection path on either side of the plate shown in FIG. 3.2 and separate beam paths shown in FIG. 3.3;

FIGS. 3.4 and 3.5 show comparative units having containers of the same dimensions as in the unit of FIG. 3.1 but rotated through 45 degrees;

FIG. 5 illustrates schematically methods for loading the sample containers of an apparatus of the invention;

FIG. 5.1 illustrates schematically how a sample container may be completely filled by providing a filling channel with an entrance above the level of the top of the sample container;

FIG. 5.2 illustrates schematically how the sample containers may be filled in a horizontal configuration and then centrifuged to force the liquid to one end of the container where it is subsequently held in place by capillary forces while the optical measurements are made;

FIG. 5.3 illustrates schematically loading of the sample containers in the horizontal configuration then rotating he plate through 90 degrees into the vertical configuration such that gravity pulls the liquid sample to one end of the container for optical measurement;

FIGS. 6.1 and 6.2 illustrate schematically embodiments of the unit of the invention with integrated channels for loading of samples and performing fluid handling operations;

FIG. 7 illustrates schematically a method of manufacture of a unit of the invention by vacuum forming two thin thermoplastic films and then joining them;

FIGS. 8.1 and 8.2 illustrate schematically embodiments of the unit of the invention in which a mirror placed under the sample plate facilitates absorption measurements whilst keeping all optical components on the same side of the sample plate;

FIGS. 9.1 and 9.2 illustrate strategies to control the temperature of the samples in multi-sample containers of the units and apparatus of the invention;

FIGS. 11.1 and 11.2 illustrate embodiments of optical systems where an imaging spectrograph and an array detector are used in combination with the apparatus of the first aspect and a suitable optical assembly to simultaneously and/or sequentially perform multiple optical measurement types using the same detector.

DETAILED DESCRIPTION OF THE INVENTION

Figure 1:
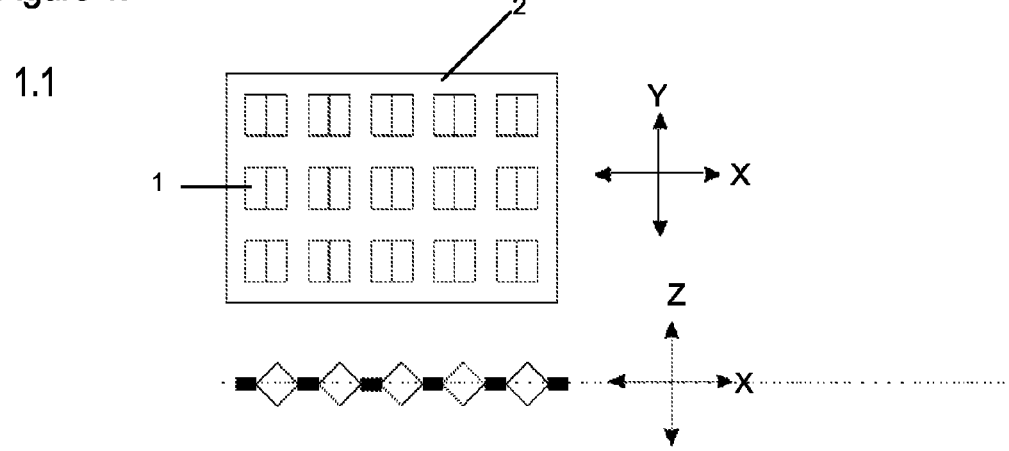
FIG. 1 illustrates schematically a multi-container sample unit according to the invention, with FIG. 1.1 showing two orthogonal views indicating the co-ordinate system and the plane of the unit and FIG. 1.2 showing vertical and horizontal configurations of the sample plate.

The present invention is concerned with apparatus for allowing multiple different types of optical measurement to be made simultaneously from an array of samples, whilst maintaining the optimum optical configuration for each measurement technique such that optical collection efficiency and signal to noise ratio for the measurements is improved.

In particular, the present inventors have developed apparatus and systems for carrying out an assay using such an apparatus which facilitates automated analysis of multiple samples, is well suited to sensitive measurements from small sample volumes due to the high efficiency delivery and collection of light which it affords and is compatible with heating and cooling of the sample volumes during measurements.

The sample containers of the unit and apparatus according to the invention suitably contain liquid samples.

Conveniently, each sample container is a polyhedron. Suitably, the container may be a triangular, square, hexagonal or octagonal shape.

In one embodiment, the containers are arranged in a regular square or rectangular array.

In a particular embodiment, the sample containers in the array are arranged such that they extend above and below the plane of the array.

Conveniently, a polyhedron such as a hexahedron or octahedron is oriented in the plane of the sample plate such that the optically transparent windows may be accessed with high optical efficiency from both above and below the plane of the sample plate.

In one particular embodiment of the invention, at least one of the windows of each container is inclined relative to the plane of the array.

Suitably, at least one of the windows of each container forms an included angle to the plane of the array of greater than zero and less than 90 degrees. In another embodiment, the container comprises a sphere with the plane of the sample plate passing through the centre of the sphere such that there is a hemisphere on each side of the plane of the plate.

In one embodiment, all of the walls of the container comprise optically transparent windows.

Suitably, the array will have a total of between 16 and 384 sample containers. In one particular embodiment, the array has 16 samples containers. In one embodiment, the outside dimensions of the array are suitably between 10 mm by 50 mm and 128 mm by 172 mm.

Conveniently, the relative positions of the sample containers in the array will correspond to standard dimensions set out by the society for biomolecular screening for 96, 384 or 1536 micro-well plates.

Preferably the cross sectional area of each of the containers will be in the range 0.04 $mm^2$ to 4 $mm^2$.

Suitably the length of each container will be in the range 1 mm to 10 mm.

The volume of a liquid sample in each of the containers is conveniently in the range 0.04 $\mu$l to 40 $\mu$l, suitably from 1 $\mu$l to 10 $\mu$l.

Preferably the cross sectional dimensions of each of the containers is sufficiently small that surface tension forces will ensure a liquid sample spans the cross sectional area of the container such that the liquid sample is in contact with all of the container windows irrespective of the orientation of the container with respect to the gravitational field. This affords the possibility of using the unit on the horizontal plane which is more readily compatible with existing automated liquid handling technology. Also, as the liquid sample is in contact with all of the container windows, the optical path length is fixed and no meniscus is formed, enabling optical absorption measurements to be made without problems; problems occurring with other optical measurement techniques are also minimised, with reduced reflection and light scatter leading to improved signal to noise for fluorescence and light scattering measurements.

In an embodiment where the cross sectional dimensions and surface properties of the containers mean that surface tension is insufficient to ensure the liquid remains in contact with the container windows when the plate is horizontal, then the plate may be loaded in a horizontal plane and then rotated through 90 degrees into the vertical plane so that the liquid sample is in contact with the windows for optical interrogation.

In one embodiment, the plate may be loaded in a horizontal configuration and then centrifuged such that the liquid sample moves to the end of the sample chamber and is subsequently held in place by capillary action during optical interrogation.

In one embodiment, each sample container has multiple non-parallel optically transparent windows.

In one embodiment, the windows are transparent in the wavelength range 250 nm-1000 nm.

A unit according to the invention comprises multiple sample containers each having multiple optical windows connected together.

Conveniently, the positions and orientations of the multiple windows of each container are arranged such that each window has an associated optical axis lying orthogonal to that window, and passing through that window, with all of the multiple optical axes being coincident at a point approximately in the centre of the sample volume defined by the container.

In one particular embodiment, at least one of the windows of each container is inclined at an angle of 45 degrees to the plane of the array.

Multiple independent optical axes which intersect at approximately the same point near the centre of the sample volume allow multiple different optical analytical techniques to be applied to the same sample volume whilst minimising any cross talk between the different techniques thus ensuring good quality signal-to-noise data from each of the techniques.

Having the effective optical sampling volume lying at approximately the centre of the sample container minimises interference in the analytical signals due to scattering or autofluorescence from the sample container windows which is particularly important for sample containers fabricated from polymeric materials where auto-fluorescence and scattering has been observed to be worse than for higher cost quartz containers. This also minimises the volume of sample required for a given signal-to-noise measurement where the noise is predominantly due to container window auto-fluorescence and scattering.

The multiple containers may be connected together by any means which allow sufficient optical access to the individual sample container to allow multiple input and output beam paths, preferably each with a large numerical aperture.

In one embodiment, the multiple containers are connected by a thin joining web. In a particular embodiment, the plane of the joining web passes approximately through the centre of the sample volumes, with optical windows lying above and below the plane of the joining web.

A thin joining web, the plane of which approximately runs through the centre of multiple sample containers, allows an array of sample containers to be constructed to form a multi-container plate where each container can be optically accessed simultaneously from above and below the plane of the array. High numerical aperture optical delivery (and hence higher collection efficiency) from multiple optical windows lying both above and below the plane of the sample plate can be achieved, thereby improving the sensitivity of optical measurements Additionally, a thin joining strip or web allows the plate to be moved readily in the plane of the plate so that each container, in turn, may be positioned such that the optical probe volume lies at the centre of each sample volume using a simple one or two axis positioning system. This avoids having to use a three axis system as would generally be required for other conventional configurations.

By configuring the unit such that the optical axis of each light beam passes approximately orthogonally to the plane of the corresponding window, reflection losses and optical distortions are minimised, thereby increasing the sensitivity of the optical measurements.

The configuration allows the container windows to be thin thus improving optical transmission, reducing optical distortions and reducing any auto-fluorescence from the container windows which might interfere with the signal from the sample. This is particularly important for small sample volumes and for polymer container windows.

The use of a thin joining web also means that the maximum surface area of each container is available for the efficient transfer of heat into or out of each sample volume which is important for a number of biochemical applications. Suitably the joining material is sufficiently thin to allow ready optical access from both sides of the plane of the sample plate, affording high numerical aperture delivery and collection of light through each of the windows of each container in the array. Conveniently, the window thickness is in the range 20-500 µm and the joining material has thickness in the range 200 µm-2000 µm.

In another embodiment, the multiple containers may be embedded in a solid material which is provided with suitably placed holes allowing optical access to the container.

In one embodiment, emitted, scattered or transmitted light is collected with a lens or lens system with a numerical aperture in the range 0.2 to 0.7

Conveniently, the entire plate is fabricated from one or two thin, optically transparent contiguous parts.

In one embodiment, the plate is thermo-formed from an optically transparent thermoplastic. Channels and functional structures may suitably be formed into the thermoformed plate in order to deliver and control delivery of fluid to the cells.

Conveniently, the plate is vacuum formed from two thin sheets of optically transparent thermo polymer which are then joined to form the enclosed containers.

In one embodiment, the plate is made from cyclic olefin co-polymer with transparency in the range 250 nm to 1000 nm.

Suitably, the sample plate is brought into contact with a thermally conductive medium such that the samples in the containers may be heated and cooled without preventing optical access to the windows of the containers.

In one embodiment the multi-container plate is contained within a metal jacket with internal profile matching the shape of the multi-container plate and holes in the metal jacket such that optical access is maintained to at least some of the sample container windows such that heating and cooling of the metal jacket results in heating and cooling of the samples in the multi-container plate.

In use, the unit described above is loaded into apparatus adapted to receive it. Illuminating light is passed into the sample volume defined by each sample container through one or more windows and the resulting scattered, emitted or transmitted light passes out of the sample container through one or more windows. The apparatus may be adapted to receive more than one unit at a time, enabling data to be captured from many samples simultaneously.

In one embodiment, the means for illuminating a sample contained in the unit comprises one or more of illuminating light sources selected from lasers, lamps or light emitting diodes.

Conveniently, multiple illuminating light sources are used and selected from 266 nm laser, 370 nm, 473 nm laser, 532 nm laser 785 nm laser, 280 nm LED, 370 nm LED, 473 nm LED, halogen lamp, Xenon lamp.

Preferably any scattered or emitted light from a sample in a sample container in the array passing out through the windows is passed to one or more optical detectors.

Suitably the samples in the containers are analysed using one or more optical analytical techniques selected from fluorescence spectroscopy, ultra-violet to visible optical absorption spectroscopy, near-infra red spectroscopy, Raman spectroscopy, light scattering.

Suitably the optical detector(s) is selected from CCD camera, CMOS camera, photo-multiplier tube, photodiode.

The emitted, scattered or transmitted light may be spectrally analysed prior to detection.

For fluorescence measurements, the included angle between the illuminating light and the emitted light collection path is suitably in the range 30 degrees and 150 degrees.

In one embodiment, for fluorescence measurements the included angle between the illuminating light and the emitted light collection path is 90 degrees or 60 degrees.

For light scattering measurements the included angle between the illuminating light and the emitted light collection path is suitably in the range 5 degrees and 179 degrees.

In one embodiment, the included angle between the illuminating light and the emitted light collection path for light scattering measurements is 90 degrees or 60 degrees For optical and infra red absorption measurements the included angle between the illuminating light beam and the transmitted light beam is suitably 180 degrees.

Preferably for Raman spectroscopy the included angle between the illuminating light and the scattered light collection path is 0 degrees, 60 degrees or 90 degrees.

Depending on the arrangement of the containers in the array, the illuminating and detecting means can be positions to either or both sides of the plane of the array.

In one embodiment, a mirror is placed below the plate and parallel to the plane of the plate such that scattered, illuminated or transmitted light passing through windows in the container on the same side of the plane of the plate as the mirror are reflected to an optical system on the opposite side of the plane of the plate.

The apparatus suitably further comprises means for heating or cooling the samples in the units in a controllable manner.

In a further aspect, the apparatus suitably comprises means for positioning the array so as to move each individual sample contained in the array to the desired location in order for analysis to be performed.

The apparatus suitably further comprises a control system, such as a computer control system, for effecting the desired assay procedure by controlling the array positioning means. Means for controlling the illuminating and detecting means in a programmed manner, such that the user can select a pre-programmed test procedure can also be provided.

Means for recording and/or displaying the results of the analysis, such as a computer display screen, may also suitably be provided.

A unit and apparatus as defined above may be combined in a system for carrying out multiple optical analytical techniques simultaneously on a sample.

The unit and apparatus according to the invention finds particular application in methods for studying protein stability.

In one embodiment, the sample is a protein in solution and UV excited fluorescence is used to monitor tertiary structure of protein, light scattering to monitor aggregation of the protein and UV-visible absorption to monitor protein concentration and tertiary structure as a function of temperature, chemical denaturant concentration or other factor that might affect the stability or aggregation properties of the protein.

Conveniently the unit is used in combination with a system of optical elements to allow light from multiple different light sources to be directed through one or more windows of each sample container.

Preferably the unit is used in combination with a system of optical components which collect scattered, emitted or transmitted light from one or more of the sample container windows and pass this light to spectral discrimination and/or detection system or systems.

In one embodiment three lasers are employed to illuminate the sample and the beams from these are arranged to be co-linear and to pass through one window of the sample containers and into the sample and any resulting scattered or emitted light from the sample is collected along a path lying at 60 degrees or 90 degrees to the incident beam path.

The unit and apparatus of the invention may suitably be used in protein science and immunodiagnostics and other assays.

Understanding the propensity of proteins to unfold and aggregate when exposed to different environments is of considerable interest to both fundamental biological research and in the development of therapeutic proteins. Very often the proteins of interest are in very short supply and so being able to simultaneously make multiple analytical measurements from a very small amount of sample while it is being stressed, for example by heating, is highly desirable as this reduces the amount of sample required to provide a given amount of information. In addition there are many examples where a researcher may want to either perform these measurements on many different proteins or on a single protein mixed in solution with a wide range of different additives and therefore an array of sample containers and automated data acquisition is highly desirable. A common way of stressing a protein is by heating it up. A typical biotechnology application of the invention would be in screening a wide range of different combinations of additives to add to a given protein in order to identify which combination gives the protein the greatest resistance to unfolding and aggregation at elevated temperatures.

Using the apparatus according to the invention, small amounts of protein may be dissolved in a wide range of different solutions with each sample being placed in an individual container in the multi-container sample plate and the samples gradually heated up. At predefined temperature increments, multiple complimentary optical analytical methods may be applied to each sample container in turn. For example, fluorescence spectroscopy can be used to monitor the tertiary structure of the protein, light scattering can be used to monitor aggregation of the protein and optical absorption can provide information about changes in the secondary structure and whether aggregated protein is precipitating.

By analysing samples using multiple orthogonal techniques simultaneously, in this way, detailed biophysical analysis of small sample volumes of proteins or other molecules may be performed, enabling biopharmaceutical development times and costs to be reduced by allowing better informed identification of lead candidates for development. Critical studies such as pre-formulation and stability studies can therefore be run much earlier in the development process, reducing the risk of late stage drug candidate attrition.

Diagnostic tests based upon the highly specific binding of antibodies to target molecules are widely used in both clinical medicine and biological research. A range of optical techniques are generally used to detect the binding of probe antibodies to the target molecule including optical absorption, fluorescence, chemi-luminescence and turbidity ('agglutination' assays). The apparatus described herein is suitable to read assays based on all the preceding readout mechanisms and indeed offers the potential to simultaneously perform multiple different assays in the same sample volume, each using a different read out mechanism. In many immuno-assay applications it is highly desirable to use the minimum amount of sample possible and to have automated running of multiple samples, for example in drug discovery applications. The use of disposable sample containers is also highly desirable since even small amounts of contamination can affect the results of the immuno-assay. The apparatus described herein fulfils these criteria.

The invention may be further illustrated by way of example only with reference to the accompanying drawings.

The apparatus of the invention comprises a planar array of optically transparent sample containers (1) physically coupled to one another in a planar configuration to form a multi-container array (2), also referred to herein as a 'sample plate'. The plane of this plate defines the XY co-ordinate plane with the Z co-ordinate lying orthogonal to this plane.

FIG. 1.1 which illustrates the co-ordinate system used in the text and the plane of the plate. The plate may be oriented horizontally or vertically with respect to the gravitational field.

The array may be of any size and arrangement. As an example, the size of the plate and the locations of the containers may conform to standards published by the society of bimolecular screening for an 8 by 12 array (giving 96 containers) or a 16 by 24 array (384 containers) or a 32 by 48 array (1536 35 containers).

The containers are fabricated from an optically transparent material such that the contents may be interrogated using optical means (3) from either or both sides of the plane of the plate (illustrated schematically in FIG. 1.2).

The containers may be of circular, square, hexagonal, octagonal or other cross sectional shape in both the XZ, XY and ZY planes such that multiple optically transparent windows are formed with different orientations with respect to the plane of the plate. If the containers are of circular cross-section then there is effectively one curved window lying on either side of the plane of the plate.

Where the cross section of the containers is a polygon then multiple optically transparent windows will be formed through which light may pass into or out of the sample volume along separate optical paths.

The angles between input and output light paths (included angle) can have a wide range of values, however, in the simplest configuration input and output beam paths will have an included angle of either 0, 90 or 180 degrees.

Some example cross-sectional shapes are shown in FIG. 2.1 together with some example light-paths in and out of the sample containers illustrating how the angle between the incoming and outgoing light beams can be varied depending on which entrance and which exit windows are used. FIG. 2.2 illustrates an example of a container shape which has an approximately hexagonal cross section in the XZ and YZ planes and a square cross-section in the XY plane giving a total of ten optical windows. FIG. 2.3 illustrates in plan and side view an octahedron-shaped container with the plane of the plate and the thin joining material passing through the bases of the two joined pyramids that make up the octahedron. In this embodiment, each individual container has four windows above (and four windows below) the sample plane. Where, as in the embodiment shown, the windows are oriented at 45 degrees to the plane of the plate, light beams passing along optical axes orthogonal to these windows (in the directions indicated by the arrows) will intersect at the centre of the octagonal volume. If multiple such containers are joined by a thin web then light can be collected from each window from each container at a collection angle close to 90 degrees (NA 0.71).

Figure 3:
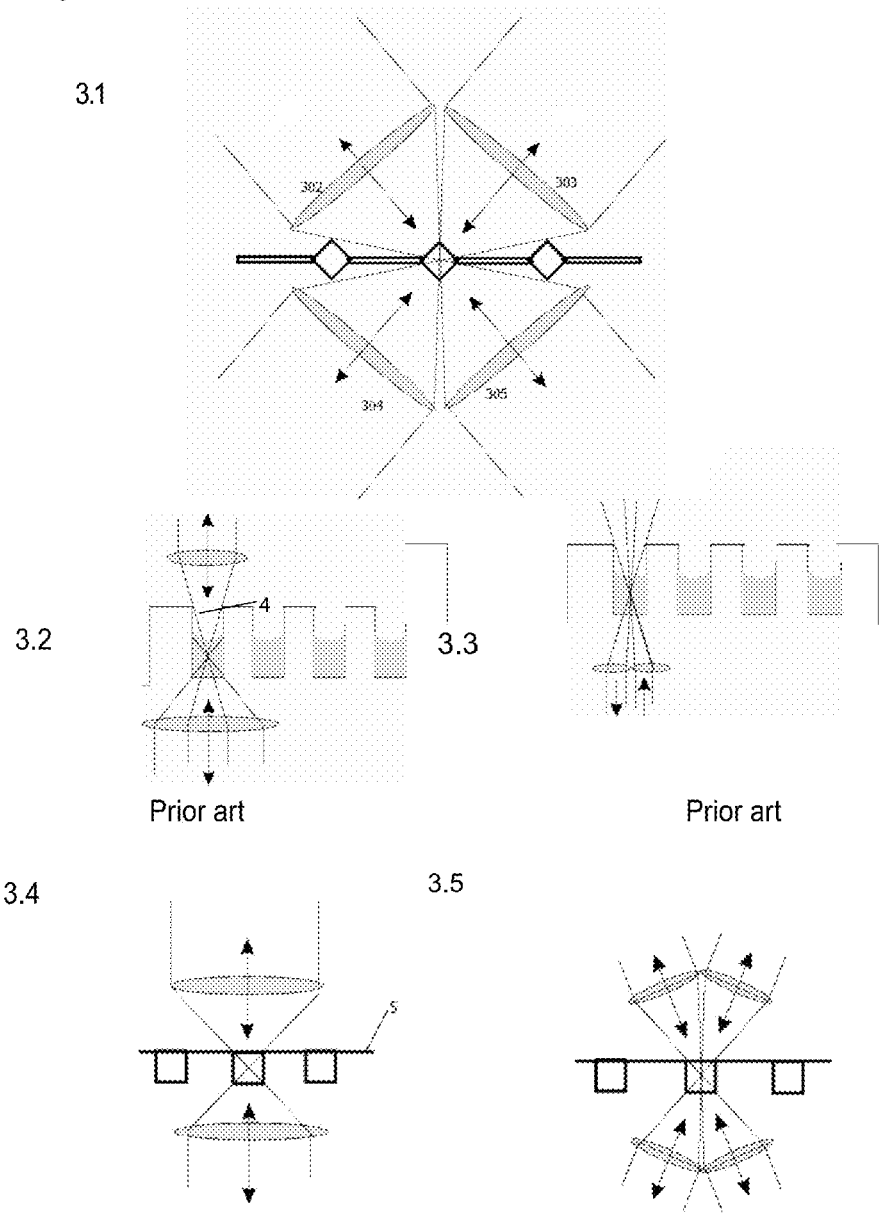
FIG. 3.1 illustrates an embodiment of the unit of the invention with square cross-section containers (rotated through 45 degrees) to give four windows, with the optical access shown.

FIG. 3.1 shows an example embodiment of the plate with square cross-section containers (rotated through 45 degrees) which gives four windows [301]. The figure also shows four lenses to deliver and collect light into the sample volume [302-305]. The amount of light collected by a lens is proportional to the numerical aperture of the lens squared where the numerical aperture is defined as the Sine of half the collection angle. It can be seen in FIG. 3.1 that the collection angle from each window is close to 90 degrees (NA=0.7) and thus collects a large amount of any emitted or scattered light. The simultaneous maintenance of four large collection angles is made possible by the thin joining material, the orientation of the windows and fact that the sample containers extend to both sides of the plane of the plate.

FIG. 3.2 shows a schematic example of a traditional style micro-titre plate with one light delivery and collection path on either side of the plate. In FIG. 3.2 the collection angle of the upper lens (4) is limited by the fact that the well is not completely filled with sample and in addition, if used in a so called epi-illumination configuration (where the input and output light share the same path) reflection of the exciting light from the sample meniscus and/or container window can significantly interfere with the signal from the sample itself, in some cases making measurements impossible. Illumination from below allows a larger collection angle but retains the problems of unwanted reflections and auto-fluorescence from the container that can obscure the signal from the sample. FIG. 3.3 shows how separate beam paths can be used for delivery and collection of light from a conventional multi-well plate, however, it can be seen that the collection angles are much smaller than those shown in FIG. 3.1 for the sample plate of the present invention. By way of illustration the collection angle in FIG. 3.1 is approximately six times greater than in FIG. 3.2 (conventional micro-titre plate) thus giving approximately 36 times greater collection efficiency per lens.

FIG. 3.4 illustrates a sample container of the same dimensions as those in the plate illustrated in FIG. 3.1 but rotated through 45 degrees and with the joining material (5) lying to one side of the wells. It can be seen that it is possible to have high NA collection but only through two of the windows, limiting both the total amount of light that can be collected and preventing the 90 degree included angle between illuminating and collected light beams which is optimum for a number of optical analytical techniques such as fluorescence and light scattering. In addition the high collection angle can only be maintained for an epi-illumination configuration with the associated disadvantages discussed previously or a straight through configuration which is ill suited to most optical analytical techniques except optical absorption. FIG. 3.5 illustrates the same plate illuminated with four lenses to enable non epi-illumination and non-straight through illumination. In this case the collection angle when four lenses are used is approximately half that of the configuration in FIG. 3.1 and thus the collection efficiency is approximately one quarter of that possible with the plate design of the present invention.

The containers may be of any size with the amount of sample required for each well being defined by the dimensions of the well. In a typical configuration the container may have a square cross section of internal diameter 1 mm and a length of 1 mm which would give a container volume of 1 μl.

Figure 4:
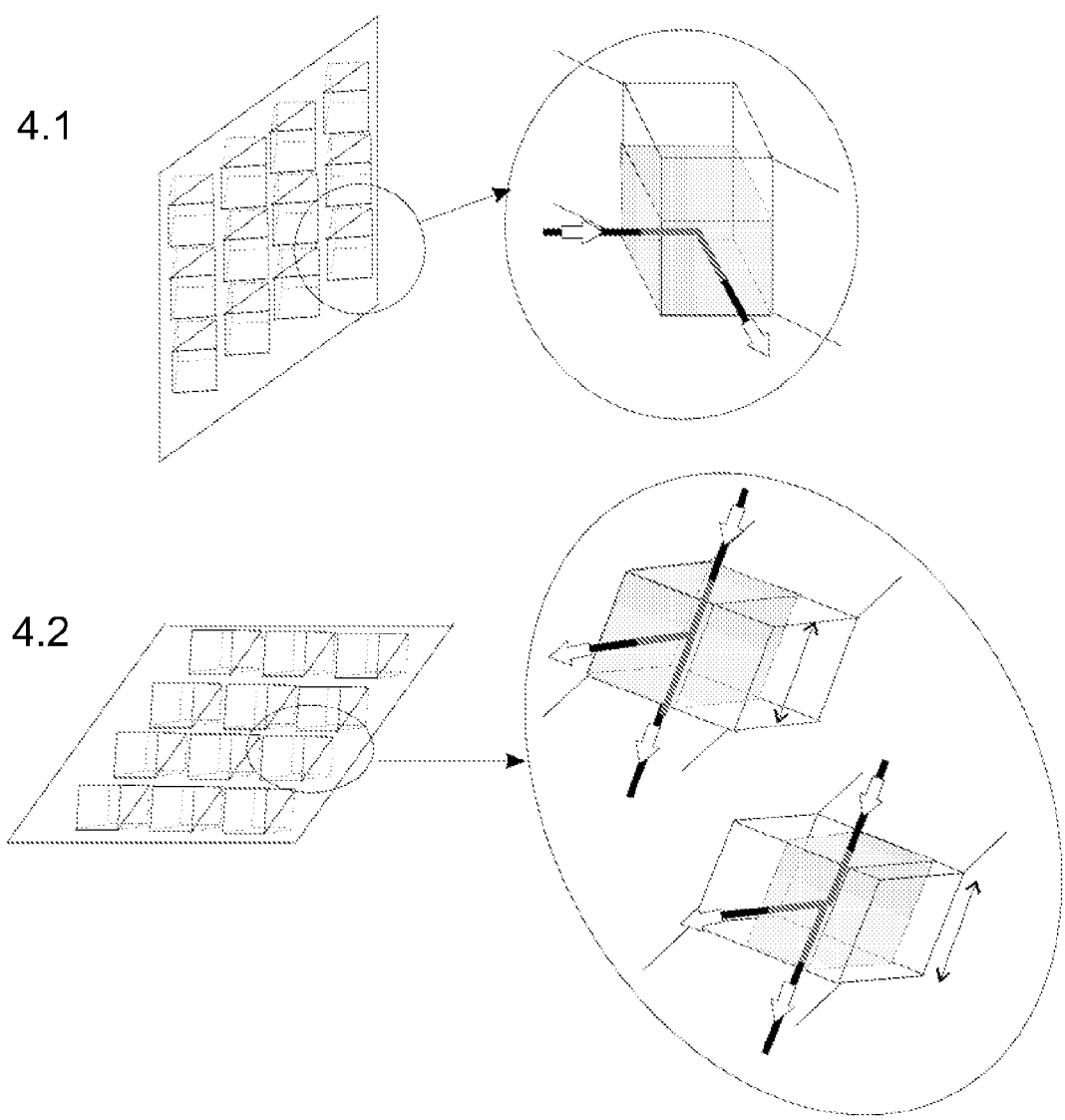
FIGS. 4.1 and 4.2 illustrate schematically the passage of light into and out of the sample in sample containers of the apparatus of the invention.

The multi-container plate may be oriented vertically (XY plane parallel to gravitational field) during measurement such that there is no air gap and meniscus between sample liquid and the container wall through which the entrance and exit light paths pass (FIG. 4.1)

When placed in a horizontal configuration if the cross sectional dimensions of the container are sufficiently small then the surface tension of the liquid sample enables the absence of an air gap and meniscus between sample liquid and the container wall through which the entrance and exit light paths pass (FIG. 4.2). Alternatively for larger sample dimensions configurations can be designed which ensure that the air-sample interface does not interfere with optical access to the sample by providing a filling channel with an entrance above the level of the top of the sample container (6) (illustrated in FIG. 5.1, direction of fill indicated by open arrows).

The plate may be configured such that it may be loaded with sample in a horizontal configuration, which ensures compatibility with conventional fluid handling equipment, and then placed in the measurement instrument in a vertical configuration (illustrated in FIG. 5.3)

If the sample containers are small then application of a centrifugal force to the plate can be used to ensure the sample is located at the end of the container (illustrated in FIG. 5.2). This is advantageous since it means that the entire container does not need to be filled for the position of the sample in the container to be known which is required during the optical measurements. For example a 1 μl liquid sample can be loaded into a 10 μl container (1 mm square cross section, 10 mm long) and centrifuged to ensure the 1 mm length of sample is located at the end of the container.

In one embodiment, the sample plate may incorporate a series of channels through which samples may flow into the containers such as those shown in FIG. 6.1 where a channel runs from a loading port (7) at the edge of the plate into the sample container and a second runs out of the chamber to allow air to leave as the container is filed. Flow may be driven by various means known to the art such as application of a centrifugal force or a pneumatic force. These channels may also contain functional structures such as splitters and mixers known to the art and applied in the field of micro-fluidics. An example simple splitting structure is shown in FIG. 6.2 in which a sample may be loaded into the main loading port (8) and is then split into nine aliquots as it passes through the channel structure.

The design of plate is particularly amenable to manufacture from vacuum formed or embossed optically transparent polymer films. A schematic illustration of the vacuum forming process is presented in FIG. 7. Two sheets of optically transparent thermo-polymer (9,10) are placed between two halves of a mould (11,12) which has female features corresponding to the desired profile of the final late (FIG. 7.1), air is then removed from the gaps between the moulds and the sheets and the polymer is then heated (vacuum indicated by arrows). When heated the polymer becomes soft and the differential in pressure forces the sheet to take on the profile of the mould (FIG. 7.2). While the polymer is still soft the two halves of the mould may then be pressed together to join the two polymer halves (FIG. 7.3) before the assembly is cooled and the finished sample plate removed from the mould (FIG. 7.4). Such a method of manufacture is advantageous as it is suitable for low cost mass production and uses only small amounts of polymer to fabricate each plate, the thin film has good optical transparency, and tends to generate less interfering auto-fluorescence than bulk material which is particularly important for small sample volumes. A thin film also allows good thermal contact between the sample inside and external heating/cooling facilitating good control of the sample temperature and rapid thermal equalisation.

Alternatively the plate may be manufactured from suitable thermo-plastic using injection moulding techniques. Manufacture using low cost materials such as transparent thermo polymers has the potential to make disposable sample plates economically viable; disposable plates are desirable in many applications since they may be more cost and time effective than washing plates and because the possibility of sample contamination is removed. A further alternative method of manufacture is to use sections of optically transparent polymer, glass or quartz tube bonded to a machined or injection moulded plate.

Another key advantage of maintaining the optimum configuration for each optical measurement type is reduced auto-fluorescence interference from the container in the optical measurements. This is particularly important for deep UV excited fluorescence and for Raman spectroscopy. This in turn has the advantage that cheaper materials may be used to manufacture the sample plate thus reducing manufacturing costs and making disposable sample plates economically viable with the associated benefits outlined above. Additionally, reduced background signal means smaller sample volumes or concentrations may be studied which is important in many applications.

In one embodiment, the sample plate is configured such that light passing through the sample container (1) is reflected off a mirror (13) lying perpendicular to the plane of the sample plate such that exiting light is reflected through 90 degrees. FIG. 8 illustrates the use of a mirror to facilitate absorption measurements. This may, for example be used to enable absorption spectroscopy to be performed whilst keeping all optical components other than the mirrors on the same side of the plane of the plate simplifying both the optical design and the design of sample heating and cooling systems since a heating cooling system under the sample plate does not need to be optically transparent. FIG. 8.1 shows single input path and multiple output paths, FIG. 8.2 illustrates multiple input paths with a single output path.

Conveniently, the plate may be either made from a thermally conductive material, have thermally conductive parts or be contained in a thermally conductive envelope. This may then be used to transfer heat to or from the sample in the container to facilitate temperature control of the sample. This is a common requirement in many potential biochemical applications. FIG. 9.1 illustrates a sample plate sat on a heating/cooling stage (14) with the mirror configuration described in the previous paragraph allowing optical absorption measurements to be made. FIG. 9.2 shows a sample plate enclosed in a jacket (15) made of a thermally conductive material with optical access holes provided to allow illumination and collection of light from the sample.

The present invention allows multiple different light sources to be used to simultaneously and/or serially illuminate the sample volume from multiple input directions. This is advantageous since different optical measurement types require different light source types and wavelength ranges of light.

Figure 10:
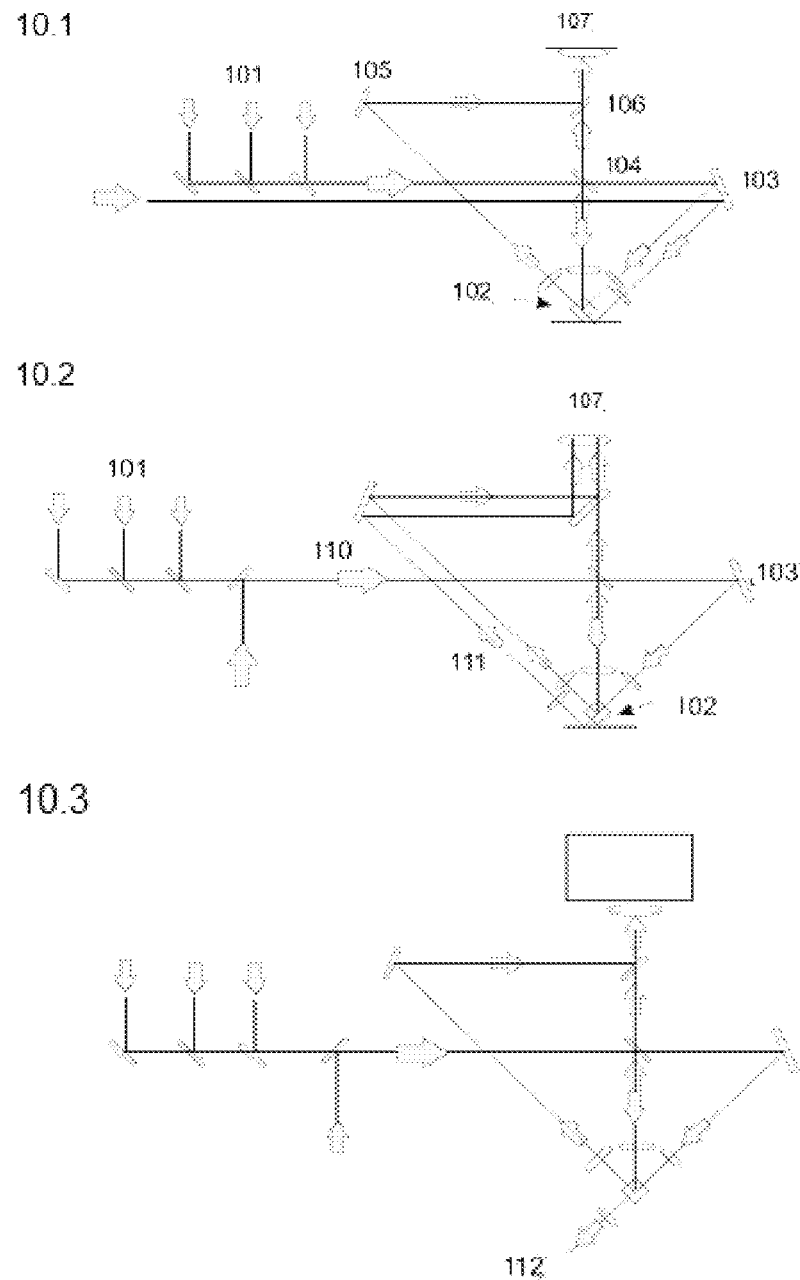
FIGS. 10.1, 10.2 and 10.3 show different optical configurations for use in combination with the units and apparatus of the invention to allow multiple different optical measurement techniques to be performed simultaneously on a sample in a sample container.

An optical configuration is disclosed which allows exiting light to be collected simultaneously or serially at multiple included angles with respect to the input light. This is advantageous since the optimum optical configuration is different for different optical measurement techniques and also allows multiple measurement types to be made simultaneously, illustrated schematically in FIG. 10. As shown in FIG. 10.1, one or more illumination sources [101] pass above and parallel to the plane of the sample plate [102] to a mirror [103] which directs the beam down through one of windows of one of the sample containers. Alternatively the illuminating light beam may be directed by an alternative optical beam splitter or filter [104] at a different angle through a different window in the sample container. Scattered or emitted light is passed to another mirror [105] and then to a further optical beamsplitter or mirror [106] to the optical detection system [107]. Alternative embodiments of this basic configuration are shown in FIGS. 10.2 (single input, dual output) and 10.3 (single input path, dual output path, no mirror).

In FIG. 10.2 all illumination sources share a coincident optical path into the sample volume [110] and the transmitted and emitted/scattered light passes to the detection system along two separate but parallel optical paths [111].

In the alternative embodiment of FIG. 10.3 the illuminating light from multiple sources is delivered along a single coincident light path and collected at multiple angles. In this embodiment, however, no mirror is placed under the sample plate and transmitted light passes to a separate detector system [112].

Different optical measuring types compatible with the present invention with indications of the type of light source and optimum configuration of input and output light paths are listed in the Table 1 below:

TABLE 1

| Optical measurement method | Typical light source | Wavelength range | Optimum Included angle between input and output light |
|---|---|---|---|
| Fluorescence spectroscopy | Laser or filtered lamp | narrow | 90 degrees [a] |
| Light scattering | Laser | narrow | 90 degrees or multiple angles [b] |
| Optical absorption spectroscopy (UV-visible) | Lamp | broad | 180 degrees |

TABLE 1-continued

| Optical measurement method | Typical light source | Wavelength range | Optimum Included angle between input and output light |
|---|---|---|---|
| Optical absorption spectroscopy (NIR) | Lamp | broad | 180 degrees |
| Raman spectroscopy | Laser | narrow | 90 degrees |

[a] 90 degree configuration results in less exciting light interference in spectrum and reduced auto-fluorescence from the sample container
[b] 90 degree configuration reduces background signal due to reflections at container walls. Multiple angles can give information about larger particle size.

The output light may be passed to one or more types of spectral analysis and detection systems. The light may be directed to multiple analysis and detection channels with each being designed for one or more optical measurement types (Example presented in FIG. 10.3). Alternatively a single analysis and detection channel may be employed that is suitable for all the optical measurement types being employed (examples presented in FIGS. 10.1 and 10.2).

In one embodiment of the invention an imaging spectrograph and an array detector such as a CCD camera may be used in combination with the sample plate and a suitable optical assembly to simultaneously and/or sequentially perform multiple optical measurement types using the same detector, illustrated schematically in FIG. 11.

FIG. 11.1 schematically illustrates the area of an array detector at the focal plane of an imaging spectrograph. The wavelength range of each of the optical analysis techniques are different and may therefore be read out simultaneously in a single exposure of the array detector. FIG. 11.1 shows how UV absorption, fluorescence, light scattering and Raman spectra can all be recorded simultaneously (as shown, region A is UV absorption, region B is fluorescence, region C is light scattering and region D is a Raman spectrum).

In the alternative configuration of FIG. 11.2 the spectrally separate light for the different techniques is arranged on the array detector in perpendicular stripes so that once again all of the information may be acquired in a single exposure of the detector.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise. Preferred features of each aspect of the invention may be as described in connection with any of the other aspects.

The invention claimed is:

1. A unit comprising an array of sample containers, said containers being connected together and arranged in a planar configuration, each container having multiple optically transparent windows arranged such that the sample contained therein is configured for interrogation using simultaneous multiple optical analytical techniques, the array of containers being configured so as to allow optical access to the windows of each container in the array, wherein at least one of the windows of each container is inclined to the plane of the array and the sample containers are connected by a joining web, the sample containers and joining web being arranged such that each individual sample container has an inclined window lying above and below the joining web.

2. A unit according to claim 1 wherein each sample container comprises a polyhedron.

3. A unit according to claim 1 wherein each sample container comprises a cylinder or sphere.

4. A unit according to any one of claims 1 to 3 wherein the cross sectional dimensions of each of the containers is sufficiently small that surface tension forces will ensure a liquid sample spans the cross sectional area of the container such that the liquid sample is in contact with all of the container windows irrespective of the orientation of the container with respect to the gravitational field.

5. A unit according to claim 1 wherein each sample container has multiple non-parallel optically transparent windows.

6. A unit according to claim 1 wherein each of the walls of the containers comprise optically transparent windows.

7. A unit according to claim 1 wherein the array comprises thermally conductive material.

8. A unit according to claim 1 further comprising one or more channels through which samples may be filled into the containers.

9. A unit according to claim 1 formed from an optically transparent thermoplastic material.

10. A unit according to claim 1 further comprising a mirror, the mirror being located below the array of containers and parallel to the plane of the array.

11. An apparatus according to claim 1 wherein the array is enclosed in a thermally conductive jacket with optical access holes being provided in the jacket to allow illumination and collection of light from the sample.

12. A unit according to claim 1 wherein at least one of the windows of each container forms an included angle to the plane of the array of greater than zero and less than 90 degrees.

13. A unit according to claim 12 wherein the at least one window forms an included angle to the plane of the array of 45 degrees.

14. A unit according to claim 1 wherein the sample containers are embedded in a solid material which is provided with holes allowing optical access to the container.

15. An apparatus for carrying out simultaneous multiple optical analytical techniques on a sample, said apparatus comprising means for receiving a unit according to claim 1, means for illuminating a sample contained in said unit and means for detecting light emerging from said sample.

16. An apparatus according to claim 15 adapted to receive more than one unit according to claim 1.

17. An apparatus according to claim 15 or claim 16 further comprising means for heating or cooling the samples in the unit or units.

18. An apparatus according to claim 15 further comprising means for positing the unit to enable the individual sample containers to be located at the required location for the analysis to be performed.

19. An apparatus according to claim 18 further comprising means for controlling the unit positioning means.

20. An apparatus according to claim 15 further comprising means for recording and/or displaying the results of the analysis.

21. A method of analyzing multiple samples by introducing each individual sample into an individual container of a unit according to claim 1, loading said unit into an apparatus according to claim 15, illuminating the samples and detecting light emerging therefrom.

22. A method according to claim 21 wherein an individual sample is simultaneously illuminated with multiple different light sources.

23. A method according to claim 21 wherein an individual sample is serially illuminated with multiple different light sources.

24. A method according to claim 21 wherein the sample is illuminated from multiple input directions.

25. A method according to claim 21 wherein the emerging light is collected simultaneously or serially at multiple included angles with respect to the input light.

26. A method according to claim 21 wherein the samples in the containers are analysed using one or more optical analytical techniques selected from fluorescence spectroscopy, ultra-violet to visible optical absorption spectroscopy, near-infra red spectroscopy, Raman spectroscopy, light scattering.

27. A method according to claim 21 wherein the illuminating light is selected from one or more sources selected from lasers, lamps or light emitting diodes.

28. A method according to claim 21 wherein the sample is a protein in solution.

\* \* \* \* \*